US00PP25924P2

(12) United States Plant Patent
Verschoor

(10) Patent No.: US PP25,924 P2
(45) Date of Patent: Sep. 22, 2015

(54) ***VERONICA* PLANT NAMED 'BICOLOR EXPLOSION'**

(50) Latin Name: ***Veronica* hybrid**
Varietal Denomination: Bicolor Explosion

(71) Applicant: Jan Verschoor, Haarlem (NL)

(72) Inventor: Jan Verschoor, Haarlem (NL)

(73) Assignee: A. VERSCHOOR HORTICULTURE IMPORT-EXPORT B.V, Haarlem (NL)

( * ) Notice: Subject to any disclaimer, the term of this patent is extended or adjusted under 35 U.S.C. 154(b) by 103 days.

(21) Appl. No.: 13/999,116

(22) Filed: Jan. 15, 2014

(51) Int. Cl.
*A01H 5/02* (2006.01)

(52) U.S. Cl.
USPC ..... Plt./251

(58) Field of Classification Search
USPC ..... Plt./251
See application file for complete search history.

*Primary Examiner* — Susan McCormick Ewoldt
(74) *Attorney, Agent, or Firm* — Penny J. Aguirre

(57) ABSTRACT

A new cultivar of *Veronica*, 'Bicolor Explosion', characterized by its compact, upright and strong plant habit, its flowers that are bi-colored purple and violet, its freely branching inflorescences, and its tolerance to powdery mildew.

2 Drawing Sheets

Botanical classification: *Veronica* hybrid.
Variety denomination: 'Bicolor Explosion'.

BACKGROUND OF THE INVENTION

The present invention relates to a new and distinct cultivar of *Veronica* of hybrid origin and will be referred to hereafter by its cultivar name, 'Bicolor Explosion'. 'Bicolor Explosion' represents a new herbaceous perennial grown for landscape use.

The new cultivar, 'Bicolor Explosion', was discovered by the Inventor in summer of 2010 as a naturally occurring branch mutation of *Veronica* 'Blue Explosion' (U.S. Plant Pat. No. 22,497) in a trial bed in Haarlem, The Netherlands.

Asexual propagation of the new cultivar was first accomplished by softwood cuttings by the Inventor in summer of 2010 in Haarlem, The Netherlands. Asexual propagation by division and softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bicolor Explosion' as a unique cultivar of *Veronica*.

1. 'Bicolor Explosion' exhibits a compact, upright and strong plant habit.
2. 'Bicolor Explosion' exhibits flowers that are bi-colored purple and violet.
3. 'Bicolor Explosion' exhibits freely branching inflorescences.
4. 'Bicolor Explosion' exhibits tolerance to powdery mildew.

The parent plant of 'Bicolor Explosion', 'Blue Explosion', differs from 'Bicolor Explosion' in having flowers that are blue in color and not bi-colored. 'Bicolor Explosion' can be most closely compared to the *Veronica* cultivars 'Blue Bomb' (U.S. Plant Pat. No. 22,509) and 'Pink Explosion' (U.S. Plant Pat. No. 22,592). Both cultivars are similar to 'Bicolor Explosion' in having a compact, upright plant habit and in flowering from June into September in Haarlem, The Netherlands. 'Blue Bomb' differs from 'Bicolor Explosion' in having less branched and less compact inflorescences, in being shorter in height, in having single-colored flowers, and in having stems that are narrower in width. 'Pink Explosion' differs from 'Bicolor Explosion' in having single-colored flowers that are light pink in color.

BRIEF DESCRIPTION OF THE DRAWINGS

The accompanying colored photographs illustrate the overall appearance and distinct characteristics of the new *Veronica*. The photographs were taken of nine month-old plants of 'Bicolor Explosion' as field grown in Haarlem, The Netherlands (place in a container for the photographs).

The photograph in FIG. 1 provides a side view of a plant of 'Bicolor Explosion' in bloom.

Figure 1:
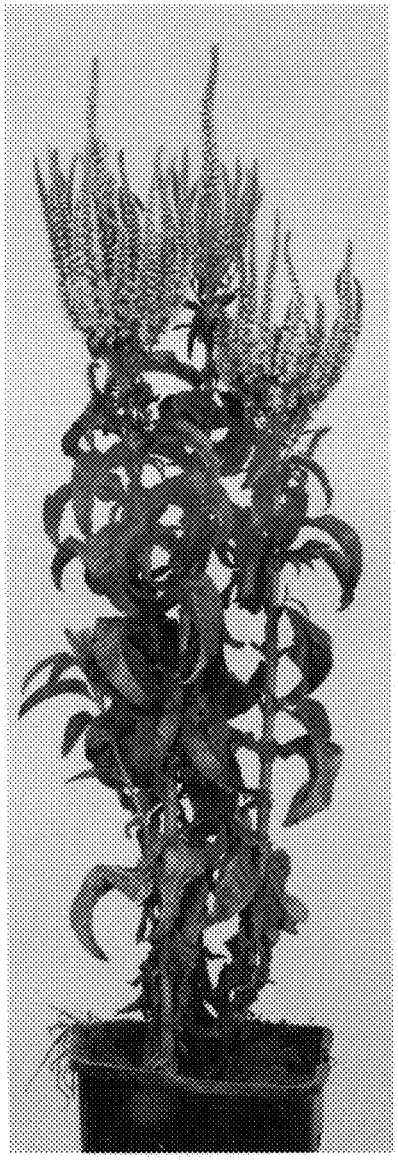
Figure 2:
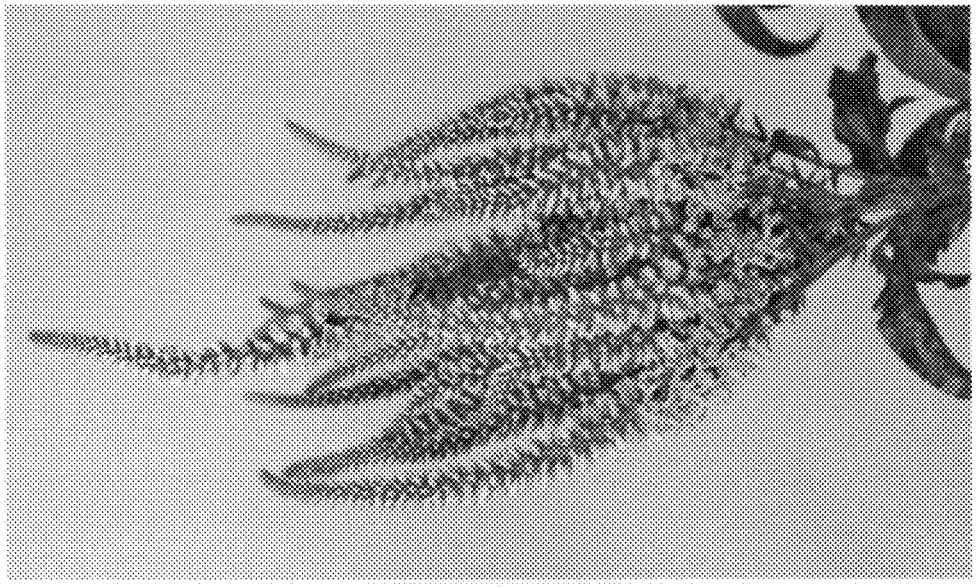

The photograph in FIG. 2 provides a close-up view of an inflorescence of 'Bicolor Explosion'.

Figure 3:
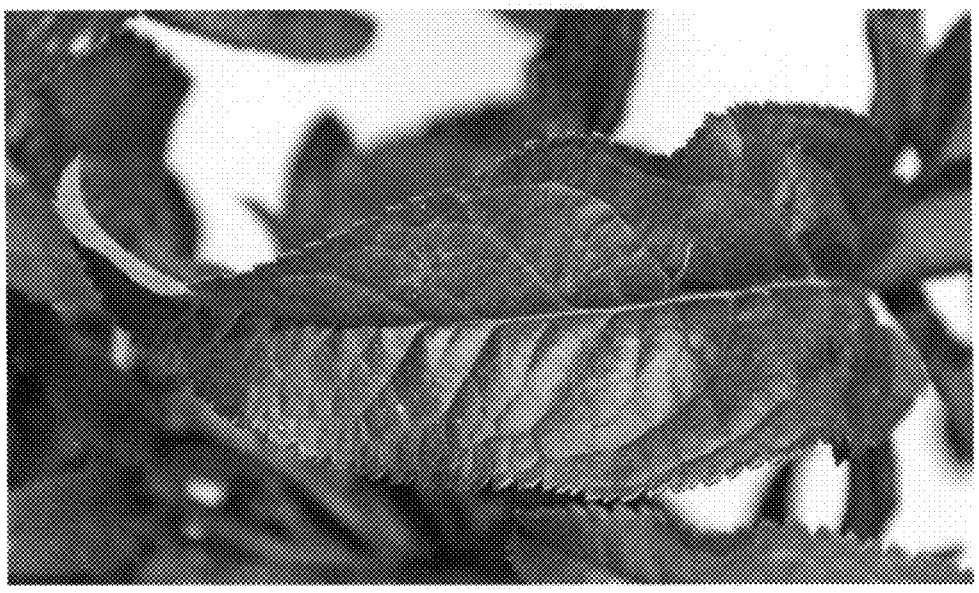

The photograph in FIG. 3 provides a close-up view of the foliage of 'Bicolor Explosion'.

The colors in the photographs may differ slightly from the color values cited in the detailed botanical description, which accurately describe the colors of the new *Veronica*.

DETAILED BOTANICAL DESCRIPTION

The following is a detailed description of the new cultivar as observed for a plant about 9-months in age as field grown outdoors in Haarlem, The Netherlands. The plants were grown under average day temperatures of 15° to 30° C. and average night temperatures of 6° to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from June to September.

*Plant type*.—Herbaceous perennial.

*Plant habit*.—Compact, upright and strong plant habit.

*Height and spread*.—Reaches about 75 cm in height and 25 cm in spread.

*Hardiness*.—At least hardy in U.S.D.A. Zone 4.

*Diseases*.—Has shown tolerance to powdery mildew.

*Root description*.—Fibrous and fine.

*Propagation*.—Division or softwood cuttings.

*Growth rate*.—Moderate.

Stem description:

*Shape*.—Round.

*Stem quantity*.—Average of 3 main stems.

*Stem color*.—144A.

*Stem size*.—Average of 8 mm in diameter and 47.3 cm (excluding inflorescence) in length, internode is 3.2 cm in length.

*Stem surface*.—Slightly glossy and moderately covered with pubescence hairs; an average of 5 mm in length and 157D in color.

*Stem aspect*.—Held at an average angle of 85° to soil level.

*Branching habit*.—Moderately branching from the base.

Foliage description:

*Leaf division*.—Simple.

*Leaf arrangement*.—Opposite.

*Leaf shape*.—Narrow ovate to lanceolate, slightly to moderately curved and slightly carinate.

*Leaf size*.—An average of 9.9 cm in length and 3.7 cm in length.

*Leaf number*.—Average of 30 per branch.

*Leaf base*.—Truncate.

*Leaf apex*.—Acute.

*Leaf margin*.—Finely serrate with an average of 6 teeth per cm.

*Leaf venation*.—Pinnate, upper surface 144A in color, lower surface 144B in color.

*Leaf surface*.—Upper surface moderately glossy, lower surface slightly glossy, both surfaces moderately to densely covered with very short pubescent hairs; 157D in color, average length of hairs on upper side is 1 mm, average length of hairs on lower surface is 2 mm.

*Leaf color*.—Young upper surface; 143A, young lower surface; color between 143B and 144A, mature upper surface; color between N137B and 147A, mature lower surface; 147B.

*Leaf attachment*.—Sessile.

Flower description:

*Inflorescence type*.—Compound racemes of rotate-shaped flowers.

*Lastingness of inflorescence*.—Individual flowers last 3 to 4 days, inflorescence lasts about 10 days, blooms from bottom of raceme towards apex.

*Inflorescence size*.—Average of 21.5 cm in length and 10.6 cm in diameter.

*Flower type*.—Outward and campanulate in shape.

*Flower number*.—Average of 3,700 per compound inflorescence and 11,000 per plant.

*Flower fragrance*.—None.

*Flower buds*.—Ovate in shape, about 5 mm in length and 2 mm in diameter, color is 75D and 76D, marbled and striped with N88C.

*Flower size*.—About 8 mm in depth and 8 mm in diameter.

*Peduncles*.—Primary peduncle; 21.3 cm in length and 3 mm in diameter, held vertically, strong, and 138A to 138B in color, secondary peduncles; 15.1 cm in length and 2 mm in diameter, held at an average angle of 40°, strong and 138A to 138B in color.

*Pedicels*.—An average of 1.5 mm in length and 0.5 mm in width, held at an average angle of 45°, strong, 138A to 138B in color.

*Calyx*.—Rotate in shape, an average of 3 mm in length and 3 mm in diameter.

*Sepals*.—4, rotate, narrow ovate in shape, base is cuneate with lower 5% fused, matte and glabrous surfaces, entire margin, acute apex, lower sepals 3 mm in length and 1 mm in width, upper sepals 1.75 mm in length and 1 mm in width, color; immature and mature upper surfaces 141A, immature and mature lower surfaces 138B.

*Petals*.—4, campanulate in shape, obtuse apex, lower 40% fused, entire margin, color; upper side when opening; 75C, marbled and striped with N88B to N88C, lower side when opening; 75C to 75D, marbled and striped N88B to N88C, upper surface when fully opened; 75C, marbled and striped N88B to N88C, lower surface fully opened; 75C to 75D, marbled and striped N88B to N88C, lower petal 2.5 mm in width, lateral petals 3 mm in width, upper petal 4 mm in width and all are 5 mm in length.

Reproductive organs:

*Gynoecium*.—1 Pistil 6 mm in length, style is about 55 mm in length and N78C to N78D in color, stigma is clavate in shape and 77A in color, ovary is superior 145A in color.

*Androecium*.—2 stamens, filament is about 5 mm in length and between 85C and N88D in color, anthers are dorsifixed and elliptic in shape, about 2 mm in length and N77B to N77D in color, pollen is moderate in quantity and 4C in color.

*Fruit*.—Fruit and seed production was not observed under the conditions tested.

It is claimed:

1. A new and distinct cultivar of *Veronica* plant named 'Bicolor Explosion' as herein illustrated and described.

* * * * *